United States Patent
Cherdshewasart

(12) 
(10) Patent No.: US 6,673,377 B1
(45) Date of Patent: Jan. 6, 2004

(54) EXTRACTS DERIVED FROM PUERARIA MIRIFICA, BUTEA SUPERBA AND/OR MUCUNA COLLETTII AND EXTRACTION THEREOF

(75) Inventor: Wichai Cherdshewasart, Bangkok (TH)

(73) Assignee: Cheil Jedang Corporation, Seoul (KR)

(*) Notice: Subject to any disclaimer, the term of this patent is extended or adjusted under 35 U.S.C. 154(b) by 0 days.

(21) Appl. No.: 09/830,455
(22) PCT Filed: Aug. 28, 2000
(86) PCT No.: PCT/KR00/00961
§ 371 (c)(1), (2), (4) Date: Aug. 6, 2001
(87) PCT Pub. No.: WO01/15718
PCT Pub. Date: Mar. 8, 2001

(30) Foreign Application Priority Data

Aug. 27, 1999 (TH) .............................................. 052443

(51) Int. Cl.$^7$ .............................................. A61K 35/78
(52) U.S. Cl. ........................ 424/725; 424/773; 424/774; 424/779
(58) Field of Search ................................. 424/725, 773, 424/774, 779

(56) References Cited

U.S. PATENT DOCUMENTS 5,401,503 A * 3/1995 Murayama
5,560,913 A * 10/1996 Kupper

FOREIGN PATENT DOCUMENTS

| CA | 1199276 | * | 1/1986 |
| DE | 3130895 | * | 2/1983 |
| GB | 785987 | * | 11/1957 |
| JP | 61122217 | * | 6/1986 |

OTHER PUBLICATIONS

U.S. patent application Publication No. US 2001/0014311 A1 *External Preparation For Skin*, by Hoshino et al. Aug. 16, 2001.
Cain, J. Nature. 1960. Vol 188, pp. 774–777.*
Kashemsanta et al. Proc. Pacific Sci. Congr. Pacific Sci. Assoc., 9th. 1963. pp. 37–40, CAPLUS Abstract enclosed.*
Ingram et al. Z. Naturforsch. 1986. vol. 41, No. 4, pp. 403–408.*
Jones et al. J. Endocrinol. 1961. vol. 22, pp. 303–312, CAPLUS Abstract enclosed.*
Hoffman, D. The Complete Illustrated Herbal. 1996. Barnes and Noble Books, pp. 20–21.

* cited by examiner

Primary Examiner—Christopher R. Tate
(74) Attorney, Agent, or Firm—Birch, Stewart, Kolasch & Birch, LLP

(57) ABSTRACT

The present invention relates to extracts derived from *Pueraria mirifica, Butea superba* and/or *Mucuna collettii* and extraction thereof, foods, beverages, pharmaceutical products and/or cosmetics containing the extracts as an active ingredient and manufacturing thereof. The extracts isolated from the said plants contain higher concentration of isoflavones. The products produced from composition containing the extracts considerably increase a resilience and gloss of skin at its application in human body.

6 Claims, No Drawings

EXTRACTS DERIVED FROM *PUERARIA MIRIFICA*, *BUTEA SUPERBA* AND/OR *MUCUNA COLLETTII* AND EXTRACTION THEREOF

TECHNICAL FIELD

The present invention relates to extracts derived from *Pueraria mirifica* (white Kwao krua), *Butea superba* (red Kwao Krua) and/or *Mucuna collettii* (black Kwao Krua), an extraction process therefor, foods, beverages, pharmaceutical products and/or cosmetics containing the extracts as active ingredients, and a process for manufacturing the same.

BACKGROUND ART

*Pueraria mirifica*, a leguminous plant found mainly in Thailand, was introduced to the West in the 1930s and has been used as a Thai folk medicine for invigorating sexual activities (Nature, Dec. 3, 1960, 774). Particularly, its tubers have long been used for invigorating post-menopausal females.

*Butea superba* is also a leguminous plant found mainly in Thailand. This plant provides red sap and its tubers have long been used as a raw material for invigorating males in Thailand.

*Mucuna collettii* is a tall leguminous plant found mainly in the subtropical zones. When being cut and exposed to the air, all parts of this plant turn black. Likewise, its roots have long been used as a folk medicine for invigorating males.

In those plants are found 25 or more compounds, including miroesterol, diadzin, diadzein, genistin, genistein, beta-sitosterol, stigrmsterol, mirificoumestan, kwarkhurin, mirificine, long chain alcohols, and 5-dioxyisoflavone. Particularly, those plants are found to contain phytoestrogen in far larger quantities than do other leguminous plants.

Isoflavones are distributed in a variety of plants and extensively found particularly in such leguminous plants as soybean, arrowroot and alfafa. Isoflavones are termed phytoesterogens on the grounds that not only do these compounds have structures similar to those of endogenous estrogens, but also their physiological actions bring about the same effects as those of estrogens. Phytoestrogens, however, show insignificant physiological activity compared with estrogens. Where phytoestrogens are ingested for a long period of time, it is reported that estrogen hormone-like functions are exerted in the body (Bingham S A, Atkinson C, J. Nutr 1988 79(5) 393–406). In terms of subgroups, phytoestrogens may be broken down into coumestrol, genistgein, formonetin, diadzein, biochanin A, most of which are based on isoflavone.

There was reported one interesting study concerning phytoestrogen, in which attention was paid to the fact that Japanese women suffer from less serious menopausal diseases than do Western women. This has been revealed to be attributed to the diet of the Japanese, who consume soybean related foods containing much of phytoestrogen. Now, the use of phytoestrogen in overcoming menopausal disease is now under extensive study. Genistein, a phytoestrogenic material which can be extracted from leguminous plants, for example, is prescribed to overcome a menopausal disease. This compound is also used to prevent breast cancer or cardiovascular diseases. Additionally, diosgenin, a precursor to progesterone which is responsible for the menstrual cycle, is now commercially available as a cream formulation while being extracted from Mexican wild yams. There have successively been reported noteworthy research results on the effects of phytoestrogen on the reduction of breast cancer attack rate. In the case of Asian women, they are attacked by breast cancer, ovarian cancer, and uterine cancer less than women of the other regions since they have long consumed foods prepared from leguminous plants, which contain much phytoestrogen (Adlercreutz H, Honjo H., Am. J. Clin. Nutri. 1991, 54(6), 1093–1100).

Furthermore, phytoestrogen is known to be of anti-oxidative activity as well as being active in preventing or improving osteoporosis (Tsutsmi N, Biol. Pharm. bull 1995, 18(7) 1012–1015). In vivo, phytoestrogen binds to an estrogen receptor, showing an estrogen agonist or antagonist activity. The level at which estrogen is produced in vivo can be elucidated with the affinity for the binder. At the time of menopause, because estrogen is produced in a very small quantity, phytoestrogen's action may be relatively increased. Generally, phytoestrogen has a hormonal activity which is nothing but 1/400 to 1/1000 that of estrodiol's. However, this low activity has the advantage of showing no side effects that estrogen has. Hence, when having long been ingested, phytoestrogen is recognized as preventing the side effects estrogen can bring about, as demonstrated in various research results. Despite many research results, the accurate therapeutic mechanism and effects associated with phytoestrogen have not yet been discovered.

One of the findings disclosed as to phytoestrogen, thus far, is the physiological activity upon application to the skin. While estrogen was applied to the skin of menopausal females, who are generally in rapid progression of dermal aging, it was observed that their skin was inhibited from progressing into senility. In detail, after 6 months of the application of estrogen, the skin noticeably became resilient with a 60% improvement in the depth of wrinkles. This effect was reported to be attributed to an increase in the number of dermal collagen fibers (Schmidt J B, Binder M., Int. J. Dermatol., 1996, 35(9), 669–674).

Composing the hypoderm, elastin tissues form a network, along with collagen tissues, in the skin. Elastase, a protease which hydrolyses elastin, is known to play an important role in the anti-inflammatory mechanism. This enzyme attacks all proteins which act to maintain the backbone and shape of the connective tissues, such as elastin, collagen, proteoglycan and keratin, nonselectively as well as indiscriminately. Collagenase is known to exert its catalytic action on a limited number of substrates (Wiedow, O., Schroder, J. M., E. J. Biol. Chem. 265(25), 14791 (1990)). Exposure to UV-A makes the skin suffer repeatedly from mild inflammation in response of the catalytic action of elastase on reticular tissues and brings about damage in elastin and collagen fibers, finally making the skin sag (Motoyoshi, K., Tacenouch, M., Proceedings of the 19$^{th}$ IFSCC Congress Sydney 22–25, October 1996). Beginning in their forties, people generally have their skin rapidly decrease in resilience. From a biochemical point of view, as people grow older, elastase is increasingly active in the body, which results in destroying or aggregating a part of the elastin fibers and losing of collagen fibers (Bissett, D. L., Photochem. Photobiol., 1987, 46, 367–378). Recently, extensive research has been directed to the finding of inhibitory materials against elastase activity. For instance, cosmetics for topical application are commercially available, which contain elastase inhibitory materials in order to prevent the skin from being xeric owing to UV irritation or to inhibit the skin from progressing into senility. Particularly, plant extracts with anti-oxidation activity are under the intensive study on the retardation of dermal aging or wrinkling because they have been discovered to inhibit activity of elastase (Bizot-Foulon V., Godeat G., W. Int. J. Cos. Sci. 17, 225–264 (1995)).

DISCLOSURE OF THE INVENTION

With the knowledge that *Pueraria mirifica, Butea superba* or *Mucuna collettii,* all of which have estradiol activity 40 to 100 times as great as that of any other leguminous plant, e.g., containing phytoestrogen at a level of approximately 0.5 I. U. on average, is intimately associated with collagen, the present inventor primarily tested them for their effect on the stratum corneum in vitro.

Typically, most leguminous plants range, in phytoestrogen activity, from about 1/20,000 to 1/50 I. U. (1 I. U.=0.1 mg of estrodiol). Mica, *Butea superba* and *Mucuna collettii* showed high inhibitory activity against elastase as expected on the basis that each of them is relatively high in phytoestrogen activity (about 0.5 I. U.).

Leading to the present invention, the intensive and thorough research conducted by the present inventor, resulted in the finding that extracts derived from *Pueraria mirifica, Butea superba* and *Mucuna collettii* are not high in anti-oxidation activity, but highly inhibitory against the activity of elastase and that they have various applications in the cosmetic, pharmaceutical, and food industry.

Therefore, it is an object of the present invention to provide an extract derived from *Pueraria mirifica, Butea superba,* and/or *Mucuna collettii.*

It is another object of the present invention to provide a method for extracting pharmaceutically effective ingredient form *Pueraria mirifica, Butea superba* and/or *Mucuna collettii.*

It is a further object of the present invention to provide foods, beverages, medicines and/or cosmetics, which contain as an effective ingredient an extract derived from *Pueraria mirifica, Butea superba* and/or *Mucuna collettii.*

It is still another object of the present invention to provide a method for preparing foods, beverages, medicines and/or cosmetics, which contains as an effective ingredient an extract derived from *Pueraria mirifica, Butea superba* and/ or *Mucuna collettii.*

To achieve one of the above objects, there is provided an extract derived from *Pueraria mirifica, Butea superba* and/ or *Mucuna collettii,* wherein tubers, roots, stems, leaves and/or tissue-cultured calluses of *Pueraria mirifica, Butea superba* and/or *Mucuna collettii* are subjected to chemical extraction using water, organic solvents or mixtures thereof as an extractant.

To achieve one of the above objects, there is provided a method for preparing an extract from *Pueraria mirifica, Butea superba* and/or *Mucuna collettii,* in which tubers, roots, stems, leaves and/or tissue-cultured calluses of *Pueraria mirifica, Butea superba* and/or *Mucuna collettii* are dried in a temperature and time-controllable oven, pulverized, and immersed in water, an organic solvent or a mixture thereof, and the resulting solution was spray-, freeze- and/or vacuum-dried.

To achieve one of the above objects, there is provide a method for preparing food products, beverage products, pharmaceutical products and/or cosmetic products, comprising the steps of: extracting pharmaceutically effective ingredients from *Pueraria mirifica, Butea superba* and/or *Mucuna collettii* by drying tubers, roots, stems, leaves and/or tissue-cultured calluses of *Pueraria mirifica, Butea superba* and/or *Mucuna collettii* in a temperature and time-controllable oven, pulverizing them into pieces or powders, immersing the plant pieces or powders in water, a low alcohol with one or more hydroxyl groups, or a mixture thereof, and optionally drying the solution in a spray-drying, a freeze-drying and/or a vacuum-drying manner; and using the extract alone as a sole material or combining the extract with a base, a diluent, an additive, a dye, an active agent, a surfactant, a wetting agent, an anti-oxidant and/or other additives suitable for use in foods, beverages, pharmaceutical products and/or cosmetics at an amount of 0.1–99.9% by weight or volume based on the total weight or volume.

Herein, the products comprise the dried extract or the liquid extract at an amount of 0.1–100% and are preferably in the form selected from the group consisting of pills, capsules, packages, bottles, and boxes or in any other sealed form. Advantageously, the extract is further added with inorganic calcium or organic calcium. Preferably, the drying process is carried out at 40–90° C. for 2–9 hours in an oven.

To achieve one of the above objects, there is provided use of the fine powder, dry extract, extract and/or active ingredients derived from *Pueraria mirifica, Butea superba* and/or *Mucuna collettii* as a raw material for manufacturing cosmetics, functional cosmetics, medicinal cosmetics and pharmaceutical products suitable for use in skin care, breast care, breast firmness, breast enlargement, wrinkle removal from the breast; healthy aid foods, functional foods, beverages and pharmaceutical products suitable for use in the treatment of prostate hyperplasia; foods, beverages and pharmaceutical products suitable for use in the prevention of hypercholesterolemia and arteriosclerosis; foods, beverages and pharmaceutical products suitable for use in the treatment of erection dysfunction or malfunction; and/or foods, beverages and pharmaceutical products suitable for use in the treatment of menopausal and postmenopausal symptoms.

BEST MODES FOR CARRYING OUT THE INVENTION

A better understanding of the present invention may be obtained in light of the following examples which are set forth to illustrate, but are not to be construed to limit the present invention.

EXAMPLE 1

Preparation of *Pueraria mirifica* Extract 100 g of the tuber of *Pueraria mirifica* was cleansed, dried at 70° C. for about 5 hours by use of a hot-air drier, and pulverized. To the resulting plant pieces was added 500 mL of a mixture of methanol and water (80/20 v/v), followed by the extraction at 50° C. for about 6 hours. After being filtered, the extract was concentrated in a vacuum to remove the solvent. The concentrate was freeze-dried leaving a brownish solid which was then measured for isoflavone content. Contents of isoflavones in the extract derived from the tuber of *Pueraria mirifica* are given in Table 1, below.

TABLE 1

Contents of Isoflavones in Extract Derived from Tuber of *Pueraria mirifica*

| Isoflavone | Content (mg/100 g) |
|---|---|
| Daidzin | 51.0 |
| Daidzein | 8.1 |

TABLE 1-continued

Contents of Isoflavones in Extract Derived from Tuber of *Pueraria mirifica*

| Isoflavone | Content (mg/100 g) |
| --- | --- |
| Genistin | 12.0 |
| Genistein | 2.0 |
| Puerarin | 96.0 |

As shown in Table 1, the above processes can prepare the best quality of *Pueraria mirifica* powder. The powder prepared according to the above processes was measured to be high in its contents of isoflavone and other phytoestrogens.

Phytoestrogens obtained from the plant included miroesterol, daidzin, genistin, genistein, beta-sitosterol, stigmasterol, coumestrol, puerarin, campesterol, mirificoumestan, kwakhurin, and mirificin (Bounds and Pope, 1960; Ingham et al., 1986a; Ingham et al., 1986b; Ingham et al., 1988).

Isoflavone has potent anti-cancer activity particularly against breast cancer, rectal cancer and prostatic cancer. High contents of isoflavones in the *Pueraria mirifica* prepared in the present invention are very beneficial to the human body.

Chemical extraction of high contents of isoflavone profiles from *Pueraria mirifica* can be achieved by slicing all plant parts into pieces or grinding the plant to powder and immersing the pieces or powder in a solvent, such as water, a low molecular weight alcohol which contains one or more hydroxyl groups, and that prepared by a synthetic technique. The extract may be used as it is or may be further purified or concentrated for use.

EXAMPLE 2

Skin Lotion Containing Extract Derived from *Pueraria mirifica*

A cosmetic composition for skin lotion was prepared, which contained the *Pueraria mirifica* extract at an amount of 4.0% by weight, butylenes glycol at an amount of 4.0% by weight, sodium ethylenediaminetetraacetate at an amount of 0.001% by weight, citric acid at an amount of 0.01% by weight, ethanol at an amount of 15.0% by weight, paraoxybenzoic acid methyl at an amount of 0.1% by weight, polyoxyethylenesorbitan monostearate at an amount of 0.5% by weight, perfume at an amount of 0.2% by weight, and water at an amount of the remaining to 100% by weight. To this end, the emulsion ingredients and the aqueous ingredients were dissolved in separate baths, and then emulsified in the emulsion bath, together, followed by aging them at 30° C.

TABLE 2

Composition of Skin Lotion Containing *Pueraria mirifica* Extract

| Composition | Content (wt %) |
| --- | --- |
| *Pueraria mirifica* Extract | 4.0 |
| Butyleneglycol | 4.0 |
| EDTA-Na | 0.001 |
| Citric Acid | 0.01 |
| Ethanol | 15.0 |
| Paraoxybenzoic acid methyl | 0.1 |
| Polyoxyethylene sorbitanmonostearate | 0.5 |

TABLE 2-continued

Composition of Skin Lotion Containing *Pueraria mirifica* Extract

| Composition | Content (wt %) |
| --- | --- |
| Perfume | 0.2 |
| Purified Water | to 100 |

EXAMPLE 3

Lotion Containing Extract Derived from *Pueraria mirifica*

Using the composition shown in Table 3, below, a lotion containing an extract derived from *Pueraria mirifica* was prepared in the same manner as in Example 2.

TABLE 3

Composition of a Lotion Containing a *Pueraria mirifica* Extract

| Composition | Content (wt %) |
| --- | --- |
| *Pueraria mirifica* Extract | 4.0 |
| Cetostearyl Alcohol | 1.0 |
| Glyceryl Monostearate | 0.8 |
| Sorbitan Monostearate | 0.3 |
| Propyl Paraben | 0.1 |
| Polysorbate 60 | 1.0 |
| Mineral Oil | 5.0 |
| Cyclomethicone | 3.0 |
| Dimethicone | 0.5 |
| Allantoin | 0.1 |
| Glycerin | 5.0 |
| Propyleneglycol | 3.0 |
| Methyl Paraben | 0.2 |
| Triethanol Amine | 0.2 |
| Carbomer | 8.0 |
| Purified Water | To 100 |

EXAMPLE 4

Essence Lotion Containing Extract Derived from *Pueraria mirifica*

Using the composition shown in Table 4, below, an essence lotion containing an extract derived from *Pueraria mirifica* was prepared in the same manner as in Example 2.

TABLE 4

Composition of Essence Lotion Containing *Pueraria mirifica* Extract

| Composition | Content (wt %) |
| --- | --- |
| *Pueraria mirifica* Extract | 6.0 |
| Butylene Glycol | 4.0 |
| Glycerin | 3.0 |
| Milk Extract | 1.0 |
| Allantoin | 0.1 |
| Pantenol | 0.1 |
| EDTA-Na | 0.01 |
| Carbomer | 0.15 |
| Aqueous Collagen Sol'n | 0.5 |
| Ethanol | 6.0 |
| Polyoxyethylene Octyldodecyl Ether | 0.3 |
| Parabenzoic Acid Methyl | 0.1 |
| Triethanol Amine | 0.15 |
| Purified Water | To 100 |

EXAMPLE 5

Cream Containing Extract Derived from *Pueraria mirifica*

Using the composition shown in Table 5, below, a cream containing an extract derived from *Pueraria mirifica* was prepared in the same manner as in Example 2.

TABLE 5

Composition of Cream Containing *Pueraria mirifica* Extract

| Composition | Content (wt %) |
|---|---|
| *Pueraria mirifica* Extract | 4.0 |
| Cetostearyl Alcohol | 1.0 |
| Glyceryl Monostearate | 1.0 |
| Sorbitan Monostearate | 0.3 |
| Microcrystalline Lead | 0.2 |
| Propyl Paraben | 0.1 |
| Petrolatum | 1.0 |
| Polysorbate 60 | 1.0 |
| Mineral Oil | 5.0 |
| Cyclomethicone | 3.0 |
| Dimethicone | 0.5 |
| Avocardo Oil | 2.0 |
| Allantoin | 0.1 |
| Glycerin | 5.0 |
| Propylene Glycol | 3.0 |
| Methyl Paraben | 0.2 |
| Triethanol Amine | 0.2 |
| Carbomer | 17.2 |
| Xanthan Gum | 0.1 |
| Purified Water | To 100 |

TEST EXAMPLE 1

Application of Cosmetic Composition to the Body

The cream containing the extract from *Pueraria mirifica*, prepared in Example 5, was applied to the body and tested for improvement in skin resilience and gloss. In this regard, 44 healthy female volunteers in their twenties to fifties were selected: for 39 women, a cream containing the *Pueraria mirifica* extract was used: for 4 women, a placebo cream which contained no *Pueraria mirifica* extracts was used. The cream was applied uniformly to the whole area of the breast twice a day, preferably in the morning and evening, with a daily dosage of 2 g for 2 months. On the $3^{th}$–$5^{th}$ day after menstruation, the first application of the cream was conducted. At that time, the breast was measured for resilience. After two months of the application, a measurement was made of the resilience of the breasts of the subjects. As for breast resilience, its measurement was conducted on an area 1 cm distant from the center of a nipple in the direction of 12 o'clock, with the aid of Cutometer SEM474 (Courge+ Khazaka Electronic GmbH). The results are given in Tables 6 and 7, below.

TABLE 6

Change in Breast Resilience Between Pre- and Post-Application of Cosmetic Composition of the Invention

| Pt. No | Pre-Application (mm) | Post-Application (mm) |
|---|---|---|
| Treatment Group | | |
| 1 | 0.645 | 0.968 |
| 2 | 0.824 | 0.878 |
| 3 | 0.737 | 0.923 |
| 4 | 0.969 | 1 |
| 5 | 0.917 | 0.935 |
| 6 | 0.875 | 0.923 |
| 7 | 0.97 | 0.905 |
| 8 | 0.976 | 0.951 |
| 9 | 0.951 | 0.878 |
| 10 | 0.897 | 1.048 |
| 11 | 0.947 | 0.939 |
| 12 | 0.906 | 0.952 |
| 13 | 0.931 | 0.966 |
| 14 | 0.938 | 0.944 |
| 15 | 0.926 | 1 |
| 16 | 0.895 | 0.824 |
| 17 | 0.794 | 0.888 |
| 18 | 0.895 | 0.895 |
| 19 | 0.889 | 0.9444 |
| 20 | 0.933 | 0.974 |
| 21 | 0.938 | 0.889 |
| 22 | 0.8 | 0.82 |
| 23 | 0.889 | 0.81 |
| 24 | 0.967 | 0.965 |
| 25 | 0.929 | 0.923 |
| 26 | 0.931 | 0.939 |
| 27 | 1 | 0.882 |
| 28 | 0.875 | 0.84 |
| 29 | 0.903 | 0.951 |
| 30 | 0.964 | 1 |
| 31 | 0.967 | 0.970 |
| 32 | 0.84 | 0.941 |
| 33 | 0.811 | 0.742 |
| 34 | 0.869 | 1 |
| 35 | 0.821 | 0.824 |
| 36 | 0.517 | 0.889 |
| 37 | 0.771 | 0.967 |
| 38 | 0.880 | 0.968 |
| 39 | 0.875 | 0.882 |
| Control Group | | |
| 1 | 0.95 | 0.9 |
| 2 | 0.794 | 0.95 |
| 3 | 0.867 | 0.933 |
| 4 | 0.816 | 0.842 |
| 5 | 0.938 | 0.971 |

TABLE 7

Paired T-Test Values

| | Pre-Application | Post-Application |
|---|---|---|
| Treatment Group | | |
| Avg. | 0.881076923 | 0.921471795 |
| Variance | 0.008956336 | 0.004016681 |
| Observation No. | 39 | 39 |
| Pearson's Coeffi. Of Correlation | 0.232602588 | |
| Hypothesis Mean Difference | 0 | |
| Degree of Freedom | 38 | |
| t Static | −2.499917473 | |
| P (T <= t) One-Sided Test | 0.008428418 | |
| t Critical Value One-Sided Test | 1.685953066 | |
| P (T <= t) Two-Sided Test | 0.016856836 | |
| t Critical Value Two-Sided Test | 2.024394234 | |
| Control Group | | |
| Avg. | 0.873 | 0.9192 |
| Variance | 0.00492 | 0.0025377 |
| Observation No. | 5 | 5 |
| Pearson's Coeffi. Of Correlation | 0.266946433 | |
| Hypothesis Mean Difference | 0 | |
| Degree of Freedom | 4 | |
| T Static | −1.384052624 | |

TABLE 7-continued

Paired T-Test Values

|  | Pre-Application | Post-Application |
| --- | --- | --- |
| P (T <= t) One-Sided Test | 0.119277841 |  |
| t Critical Value One-Sided Test | 2.131846486 |  |
| P (T <= t) Two-Sided Test | 0.238555682 |  |
| t Critical Value Two-Sided Test | 2.776450856 |  |

When considering a null hypothesis that there is no difference in resilience between pre- and post-application and an alternative hypothesis that the resilience is improved after the treatment, the treatment group to which the cream containing the extract derived from *Pueraria mirifica* had been applied was measured to have a P value <0.05 at a one-sided test. Accordingly, the null hypothesis was abandoned and the breast resilience was noticeably improved. On the other hand, the control group to which no extracts from *Pueraria mirifica* were applied, although it was difficult to determine the statistics from so few subjects, was measured to have a P value >0.05 at a one-sided test. That is, the null hypothesis was accepted and no improvements were brought about in breast resilience.

In addition to breast resilience, the cream was tested for breast enlargement. In this regard, the effect of the extract from *Pueraria mirifica* on breast enlargement was determined by measuring the volumes of the breast before and after the application of the cream in an MRI machine. No remarkable breast enlargement was found from the statistics.

TEST EXAMPLE 2

Application as Food Aid or Functional Food to Pre-Menopausal Female

Extracts derived from *Pueraria mirifica* according to the present invention were used as food aids or functional foods and consumed by 97 healthy women who were pre-menopausal and 20–45 years old, as shown in Table 8, below.

TABLE 8

Medicinal Efficacy of Extract from *Pueraria mirifica* as Food Aid or Functional Food

|  | Placebo | 400 mg/day | 800 mg/day |
| --- | --- | --- | --- |
| No. of Subjects | 31 | 32 | 34 |
| Breast Pain | 31 | 14 | 32 |
| Smooth Skin | 31 | 28 | 32 |
| Hair Complexity | 31 | 24 | 30 |
| Charasma Clearness | — | 3/3 | 4/4 |
| Smooth Vaginal Secretion | 31 | 14 | 29 |
| Smooth Menstruation | 31 | 2 | 10 |
| Breast Resilience | 31 | 13 | 30 |
| Breast Enlargement | 31 | 3 | 28 |
| Hip Enlargement | 31 | 3 | 20 |

31 subjects in a placebo group were each administered 2 tapioca starch capsules a day every other day for 2 months from the first day of their menstruation. All parameters measured in this placebo group were shown not to undergo a significant change.

32 subjects in a first treatment group were each administered 2 *Pueraria mirifica* capsules, each having 200 mg, per day in the same conditions as in the placebo group. Significant improvements were brought about in various parameters, including breast or bust pain (44%) which partially resulted from breast or bust firmness and enlargement, smooth skin (88%), healthy hair (75%), charasma clearness (100%), vaginal secretion (44%), smooth menstruation (6%), breast or bust firmness (44%) and enlargement (9%), and hip enlargement (9%).

33 subjects in the second treatment group were each administered 4 *Pueraria mirifica* capsules, each having 200 mg, per day in the same conditions as in the placebo group. After 2 months of the administration, greater improvements were found in all of the parameters measured, including breast or bust pain (94%), healthy hair (88%), charasma clearness (100%), smooth vaginal secretion (85%), breast or bust firmness (94%) and enlargement (88%), and hip enlargement (59%). In some subjects, blood cholesterol levels were observed to decrease after the administration.

Consequently, food aids or functional foods comprising the extract derived from *Pueraria mirifica* can increase feminine sex appeal through improvement in skin condition, hair complexity, and breast firmness and enlargement.

TEST EXAMPLE 3

Application of Food Aid or Functional Food Containing *Pueraria mirifica* Extract to Post-Menopausal Female The extract derived from *Pueraria mirifica* in Example 1 was used as a food aid or prepared into a functional food. Six women were each administered one capsule containing 200 mg of the *Pueraria mirifica* extract a day for 21 days of one month over four months.

The subjects were 35–58 years old and suffered from fever, slightly mild delusion, xeroderma, and/or disease of menstruation or menopause. Their health was checked with blood examinations, just before and after the administration. The results are given in Table 9, below.

TABLE 9

Effect of Food Aid or Functional Food containing *Pueraria mirifica* Extract on Post-Menopausal Women

| Subject No. | Age | Pre-Consumption | | Post-Consumption | |
| --- | --- | --- | --- | --- | --- |
|  |  | Symptom | Menstruation | Symptom | Menstruation |
| 1 | 46 | Fever, Delusion | Paused | Normal | Paused |
| 2 | 52 | Fever, Delusion | Paused | Normal | Paused |
| 3 | 35 | Xeroderma | Ceased | Normal | Resumed |
| 4 | 58 | Fever | Paused | Normal | Paused |
| 5 | 49 | Fever | Continued | Normal | Continued |
| 6 | 39 | Delusion | Almost paused | Normal | Normal |

As apparent from Table 9, the extract from *Pueraria mirifica* can be useful as a food aid or a functional food with excellent therapeutic effects on menopausal symptoms such as fever, mild delusion, xeroderma, and irregular menstruation.

TEST EXAMPLE 4

Cutaneous Allergy Assay of *Pueraria mirifica* Extract

The extract derived from *Pueraria mirifica* in Example 1 was assayed as to whether it causes cutaneous allergies. The assay was conducted on six Winstar rats and six rabbits. The results are given in Table 10, below.

TABLE 10

Cutaneous Allergy Assay of *Pueraria mirifica* Extract on Winstar Rats and Rabbits

| | Animal | |
|---|---|---|
| | Winstar Rat | Rabbit |
| 1' Response | No Allergic Response | No Allergic Response |
| 2' Response | No Allergic Response | No Allergic Response |

From the results inducing no allergic response from the test animals, the extract derived from *Pueraria mirifica* according to the present invention is expected to also be safe to human skin.

EXAMPLE 6

Preparation of *Butea superba* Extract 100 g of the tuber of *Pueraria mirifica* was cleansed, dried at 70° C. for about 5 hours by use of a hot-air drier, and pulverized. To the resulting plant pieces was added 50 mL of a mixture of methanol and water (80/20 v/v), followed by the extraction at 50° C. for about 6 hours. After being filtered, the extract was concentrated in a vacuum to remove the solvent. The concentrate was freeze-dried leaving a brownish solid.

TEST EXAMPLE 5

Effect of *Butea superba* as Food Aid or Functional Food

In order to determine whether the extract prepared in Example 6 could be used as a food aid or a functional food, 142 mal patients with erection dysfunction, who were 20–55 years old, were orally administered the extract or a placebo.

The subjects in the placebo groups ingested a placebo capsule containing 200 mg of tapioca starch twice a day, e.g., after breakfast and supper. The impotence patient in a first treatment group were administered one capsule containing 200 mg of the *Butea superba* extract twice a day, e.g., after breakfast and supper, for two months while the patients in a second treatment group was administered two capsules, each containing 200 mg of the *Butea superba* extract, twice a day after breakfast and supper for the same period of time. Eight parameters related to erection dysfunction were measured and the results are given in Table 11, below.

TABLE 11

Effect of *Butea superba* on Male with Erection Dysfunction Upon Oral Administration

| | Placebo | 400 mg/day | 800 mg/day |
|---|---|---|---|
| No. of Subjects | 42 | 46 | |
| 1st Erection Day after Administration (Mean ± S.D) | 42 | 7.41 ± 1.12 | 4.16 ± 0.81 |
| Immediate Erection | 42 | 32 | 43 (+4) |
| Continuous Erection | 42 | 28 | 42 (+4) |
| Erection Maintenance for 2 min after Ejaculation | 42 | 14 | 29 (+4) |
| Weekly Frequency of Erection | 42 | 32 | 43 (+4) |

TABLE 11-continued

Effect of *Butea superba* on Male with Erection Dysfunction Upon Oral Administration

| | Placebo | 400 mg/day | 800 mg/day |
|---|---|---|---|
| No. of Intercourse/Week | 42 | 11 | 20 (+2) |
| Satisfaction in Sexual Activity | 42 | 32 | 43 (+4) |

* Five subjects were prohibited from being tested for 3–4 days owing to side effects (pain in the neck of 2 subjects and in the back of 3 subjects). After watching the development of the pain, one of them was determined to be excluded from the testing. The others consumed fresh milk every day for the time being and participated again in the testing because the pains disappeared.

There was obtained a greater therapeutic effect on erection dysfunction or malfunction when *Butea superba* was used in combination with *Mucuna collettii* than alone. Therefore, in accordance with the present invention, products comprising both *Butea superba* and *Mucuna collettii* are provided, which are useful in the treatment of erection dysfunction or malfunction.

Consequently, the extract derived from *Butea superba* according to the present invention is therapeutically effective for male sexual activity. This plant is believed to have vasodilation activity in the penis. Through this activity, *Butea superba* may be used directly or as an effective ingredient for the treatment of erection dysfunction.

To demonstrate this hypothesis, 65 males with erection dysfunction or malfunction were divided into two groups. The subjects in one group were allowed to consume a placebo capsule containing 200 mg of tapioca starch twice a day, e. g., after breakfast and supper. On the other hand, a capsule containing 200 mg of *Butea superba* was administered to the subjects of the other group, twice a day after breakfast and supper. All of them were measured for erectile function. The results are given in Table 12, below.

TABLE 12

Effect of *Butea superba* on Erection Dysfunction or Malfunction

| | Total No of Subjects | No. of Restored Males |
|---|---|---|
| Placebo | 31 | 2 |
| Treatment | 34 | 28 |

As seen in Table 12, only a few patients could have erectile ability in the placebo group while most subjects in the treatment group restored the sexual potency.

Additionally, after being administered the extract from *Butea superba*, none of the subjects suffered from prostate hyperplasia. This result was attributed to the fact that the plant contained β-sitosterol, which is reported to act as a potent preventive against prostate hyperplasia (Klipel et al. 1997). With such evidence, *Butea superba* can be also prepared into a therapeutic medicine for preventing prostate hyperplasia or a health aid food. In order to obtain more potent therapeutic effects, *Butea superba* may be combined with *Mucuna collettii*. Accordingly, a medicine based on *Butea superba* is provided for the treatment of erection dysfunction or malfunction.

TEST EXAMPLE 6

Cutaneous Allergy Assay of *Butea superba* Extract

The extract derived from *Butea superba* in Example 6 was assayed as to whether it causes cutaneous allergies. The assay was conducted on six Winstar rats. The results are given in Table 13, below.

TABLE 13

Cutaneous Allergy Assay of *Butea superba* Extract on Winstar Rats

| | |
|---|---|
| 1' Allergic Response | No |
| 2' Allergic Response | No |

From the results shown in Table 13, it is recognized that the extract derived from *Butea superba* according to the present invention can be safely applied to human skin or developed into cosmetics or medicines for topical use.

TEST EXAMPLE 7

Effect of Gel Made of *Butea superba* Extract on Erection Dysfunction 63 males were divided into two groups for testing the *Butea superba* extract for effectiveness as a therapeutic medicine for erection dysfunction. For the placebo group, gel containing no *Butea superba* was applied to the penis twice a day for one month. On the other hand, the same procedure was conducted for the treatment group, except that gel containing *Butea superba* was used. After observation, the results are given in Table 14, below.

TABLE 14

Effect of *Butea superba* on Erection Dysfunction Upon Topical Application

| | Total No. of Subjects | No. of Restored Male |
|---|---|---|
| Placebo | 31 | 1 |
| Treatment | 32 | 21 |

The restoration in the placebo group is believed to result from a psychological effect or a massage effect during the application of the gel. In contrast to those in the placebo group, may of the subjects in the treatment group could restore their sexual ability. In consequence, products for topical use, which is effective for the treatment of erection dysfunction or malfunction, can be prepared from *Butea superba*.

In order to prepare an extract powder from *Mucuna collettii*, the same process as those applied to *Pueraria mirifica* or *Butea superba* may be used. The extract powder from *Mucuna collettii* is of highly potent vasodilation activity without causing serious side effects.

Chemical extraction from these three herbs *Pueraria mirifica, Butea superba* and *Mucuna collettii* can be achieved by slicing into pieces all plant parts, including roots, tubers, stems, leaves, and calluses grown through tissue culture, and immersing the pieces or powder in a solvent, such as water, a low molecular weight alcohol which contains one or more hydroxyl groups, and that prepared by a synthetic technique. The extract may be homogeneously mixed with appropriate bases to produce cosmetics or pharmaceutical medicines for topical use. Novel mixtures were also found to exhibit transdermal penetration activity.

In addition, extracts were derived from the three herbs under a high hydraulic pressure. They are also easily mixed with other ingredients suitable for use in the preparation of beverages.

From *Pueraria mirifica, Butea superba* and *Mucuna collettii*, powders of pharmaceutically effective ingredients were prepared by a spray drying, a freeze drying or a vacuum drying process. Any of the processes is suitable to obtain high quality of extracts.

In the present invention, pharmaceutically effective ingredients can be effectively extracted from the three herbs by chemical extraction and obtained as a concentrate by distillation. The extract thus obtained according to this method exhibits high medicinal efficacy.

INDUSTRIAL APPLICABILITY

As described hereinbefore, the extracts derived from *Pueraria mirifica, Butea superba* and/or *Mucuna collettii* according to the present invention are high in their contents of isoflavones. When being applied to the human body, the cosmetics, pharmaceutical products and/or foods prepared from the extracts can bring about a great improvement in skin resilience and gloss and be useful for the treatment of erection dysfunction or malfunction. Therefore, they can find various applications in the food industry, the beverage industry, the pharmaceutical industry and the cosmetic industry.

What is claimed is:

1. An extract derived from *Pueraria mirifica* having an effect on improving breast firmness, breast enlargement and wrinkle removal from the breast, wherein said extract is prepared by the steps of:

drying tubers, roots, stems, leaves and/or tissue-cultured calluses of *Pueraria mirifica*, optionally by spray-drying, freeze-drying and/or vacuum-drying;

pulverizing the dried tubers, roots, stems, leaves, and/or tissue cultured calluses into pieces or powders and then immersing the plant pieces or powders in a mixture of methanol and water;

extracting the mixture; and filtering the resulting extract and then concentrating it in a vacuum to remove the solvent.

2. A method for preparing an extract from *Pueraria mirifica* having an effect on improving breast firmness, breast enlargement and wrinkle removal from the breast, comprising the steps of:

drying tubers, roots, stems, leaves and/or tissue-cultured calluses of *Pueraria mirifica* at 40–90° C. for 2–9 hours with a hot-air drier;

pulverizing the dried tubers, roots, stems, leaves, and/or tissue cultured calluses into pieces or powders and then immersing the plant pieces or powders in a mixture of methanol and water (80/20, v/v);

extracting said mixture at 50° C. for 6 hours; and filtering the resulting extract and then concentrating it in a vacuum to remove the solvent.

3. A method for manufacturing foods, beverages, pharmaceutical products and/or cosmetics that comprise a *Pueraria mirifica* extract having an effect on improving breast firmness, breast enlargement and wrinkle removal from the breast, said method comprising the steps of:

drying tubers, roots, stems, leaves and/or tissue-cultured calluses of *Pueraria mirifica* at 40–90° C. for 2–9 hours by use of a hot-air drier;

pulverizing the dried tubers, roots, stems, leaves, and/or tissue cultured calluses into pieces or powders, immersing the plant pieces or powders in a mixture of methanol and water (80/20, v/v) and then extracting the mixture at 50° C. for 6 hours; and using the resulting extract as a sole material or combining the extract with a base, a diluent, an additive, a dye, an active agent, a surfactant, a wetting agent, an antioxidant and/or other additives suitable for use in foods, beverages, pharmaceutical products and/or cosmetics at an amount of 0.1–99.9% by weight or volume based on the total weight or volume of the food, beverage, pharmaceutical product or cosmetic.

4. The method as set forth in claim 3, wherein said products comprise said extract at an amount of 0.1–99.9%, and are in the form selected from the group consisting of pills, capsules, packages, bottles, and boxes.

5. The method as set forth in claim 3, wherein inorganic calcium or organic calcium is further added to the food, beverage, pharmaceutical product and/or cosmetic.

6. A method of improving breast firmness, enlarging breast size, or removing wrinkles from the breast, said method comprising applying the extract according to claim 1 to said breast to improve breast firmness, enlarge breast size, or remove wrinkles from the breast.

* * * * *